United States Patent
Hasegawa et al.

(10) Patent No.: US 11,331,693 B2
(45) Date of Patent: May 17, 2022

(54) ULTRASONIC TRANSDUCER ARRAY AND ULTRASONIC PROBE

(71) Applicant: Hitachi, Ltd., Tokyo (JP)

(72) Inventors: Hiroaki Hasegawa, Tokyo (JP); Kengo Imagawa, Tokyo (JP); Shuntaro Machida, Tokyo (JP); Taiichi Takezaki, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 712 days.

(21) Appl. No.: 16/361,605

(22) Filed: Mar. 22, 2019

(65) Prior Publication Data
US 2020/0069287 A1    Mar. 5, 2020

(30) Foreign Application Priority Data
Aug. 31, 2018    (JP) .............................. JP2018-162627

(51) Int. Cl.
*A61B 8/00*    (2006.01)
*B06B 1/02*    (2006.01)

(52) U.S. Cl.
CPC ........ *B06B 1/0292* (2013.01); *B06B 2201/20* (2013.01)

(58) Field of Classification Search
CPC . B06B 1/0292; B06B 2201/20; B06B 1/0629; B06B 2201/76; A61B 8/4405; A61B 8/54; A61B 8/56; A61B 8/4494; A61B 8/4444
See application file for complete search history.

(56) References Cited

U.S. PATENT DOCUMENTS

| | | | |
|---|---|---|---|
| 6,011,683 A | 1/2000 | Dat | |
| 7,736,985 B2* | 6/2010 | Enomoto | ............ G01S 7/52079 257/E21.035 |
| 2006/0086965 A1 | 4/2006 | Sakaguchi et al. | |
| 2006/0142659 A1 | 6/2006 | Okazaki et al. | |
| 2008/0001239 A1* | 1/2008 | Enomoto | ............. G01S 7/5208 438/51 |
| 2010/0202254 A1 | 8/2010 | Roest et al. | |
| 2012/0123268 A1* | 5/2012 | Tanaka | ................. B06B 1/0292 600/443 |
| 2015/0164470 A1 | 6/2015 | Shiotani et al. | |
| 2016/0310992 A1 | 10/2016 | Van Rens et al. | |

(Continued)

FOREIGN PATENT DOCUMENTS

| | | |
|---|---|---|
| CN | 1741770 A | 3/2006 |
| CN | 1779966 A | 5/2006 |
| CN | 102412272 A | 4/2012 |

(Continued)

OTHER PUBLICATIONS

Chinese-language Office Action issued in Chinese Application No. 201910223100.3 dated Aug. 21, 2020 with English translation (10 pages).

*Primary Examiner* — Daniel Pihulic
(74) *Attorney, Agent, or Firm* — Crowell & Moring LLP

(57) ABSTRACT

Capacitors, each of which is electrically connected to a capacitor which is the cell of the CMUT mounted in a chip and is used as a DC block capacitor for protecting an amplifying circuit, are formed as many as plural aligned channels in the chip. The capacitor is an electrostatic capacitance element which is not vibrated acoustically.

12 Claims, 10 Drawing Sheets

(56) References Cited

U.S. PATENT DOCUMENTS

2020/0069287 A1* 3/2020 Hasegawa ............ A61B 8/4494

FOREIGN PATENT DOCUMENTS

| CN | 104582586 A | | 4/2015 | | |
|---|---|---|---|---|---|
| CN | 110871157 A | * | 3/2020 | ........... | A61B 8/4444 |
| EP | 2409665 A1 | * | 1/2012 | ........... | A61C 1/0015 |
| JP | 2010-535445 A | | 11/2010 | | |
| JP | 2017-508315 A | | 3/2017 | | |
| JP | 2020036252 A | * | 3/2020 | ........... | A61B 8/4444 |
| WO | WO 2015/086413 A1 | | 6/2015 | | |

* cited by examiner

ULTRASONIC TRANSDUCER ARRAY AND ULTRASONIC PROBE

BACKGROUND OF THE INVENTION

Field of the Invention

The present invention relates to an ultrasonic transducer array and an ultrasonic probe, and particularly to a technology which is effective to be applied to an ultrasonic transducer array and an ultrasonic probe using an electrostatic capacitance ultrasonic transducer manufactured by a MEMS (Micro Electro Mechanical System) technology.

Description of Related Art

An ultrasonic sensor is put to practical use in various ultrasonic inspection devices such as an ultrasonic echo diagnostic device for medical use or an ultrasonic flaw detector for nondestructive inspection.

Until now, the ultrasonic sensor has mainly used the vibration of a piezoelectric body. However, recent advances in a MEM technology have led to the development of an electrostatic capacitance ultrasonic transducer (CMUT: Capacitive Micro-machined Ultrasonic Transducer) using the MEMS technology.

In the electrostatic capacitance ultrasonic transducer, a vibrator which has a cavity part between electrodes facing each other is formed on a semiconductor substrate. In the electrostatic capacitance ultrasonic transducer, DC and AC voltages are superimposed and applied to each electrode to vibrate a membrane (flexible film) near the resonance frequency, thereby generating ultrasonic waves.

For example, a technology regarding such an electrostatic capacitance ultrasonic transducer is described in JP-A-2017-508315. In JP-A-2017-508315, an electrostatic capacitance ultrasonic transducer is disclosed which includes one cavity part between upper and lower electrodes and in which vibrators having a circular layout are arranged in a matrix shape in plan view.

The CMUT has a broadband characteristic and is capable of performing transmission/reception at various frequencies. Thus, the diagnosis areas which correspond to three or four probes in a conventional piezoelectric probe can be diagnosed by one probe including the CMUT. However, in order to ensure reception sensitivity, an amplifying circuit and a capacitor for protecting the amplifying circuit are necessarily mounted in the ultrasonic probe, and the enlargement of the probe becomes a problem.

SUMMARY OF THE INVENTION

The purpose and new features of the invention will become apparent from the description of this specification and the accompanying drawings.

Among the embodiments disclosed in this application, the summary of a representative embodiment is described briefly as follows.

In an ultrasonic transducer array which is one embodiment, a first capacitor which is a vibrator (referred to as a CMUT cell or simply a cell) of a CMUT and a second capacitor which is electrically connected to the first capacitor and is not vibrated acoustically are mounted together in the same chip.

Among the aspects disclosed in this application, the effect obtained by a representative aspect is described briefly as follows.

According to the aspect, the performance of the ultrasonic transducer array can be improved. Particularly, the ultrasonic transducer array can be miniaturized.

According to the invention, the performance of the ultrasonic probe can be improved. Particularly, an ultrasonic inspection probe can be miniaturized.

DESCRIPTION OF EMBODIMENTS

Figure 1:
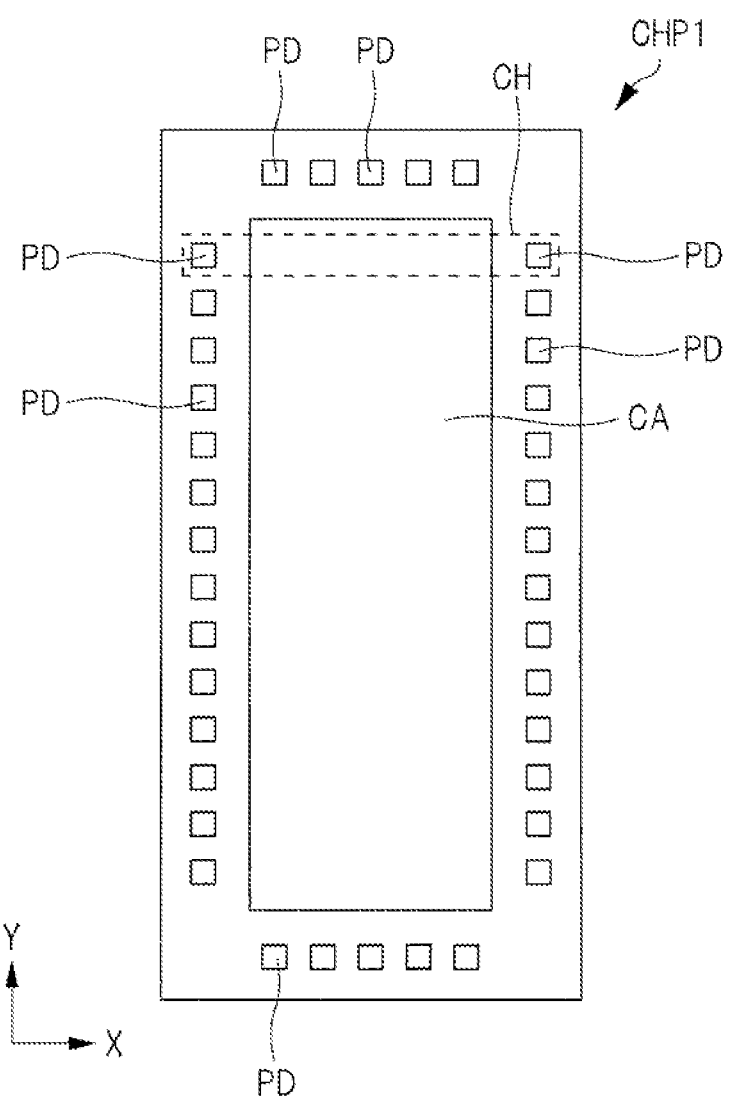
FIG. 1 is a plan view illustrating an ultrasonic transducer array which is a first embodiment of the invention.

Hereinafter, the embodiments of the invention will be described in detail based on the drawings. Incidentally, the components having the same function are denoted by the same reference numerals throughout the drawings for describing the embodiments, and the repetitive description thereof will be omitted. In addition, in the following embodiments, the description of the same or similar parts is not repeated in principle unless otherwise required.

First Embodiment

An electrostatic capacitance ultrasonic transducer configuring an ultrasonic transducer array of this embodiment is an ultrasonic transmission/reception sensor which is manufactured by using a MEMS (Micro Electro Mechanical System) technology. <Structure of Ultrasonic Transducer Array>

Figure 2:
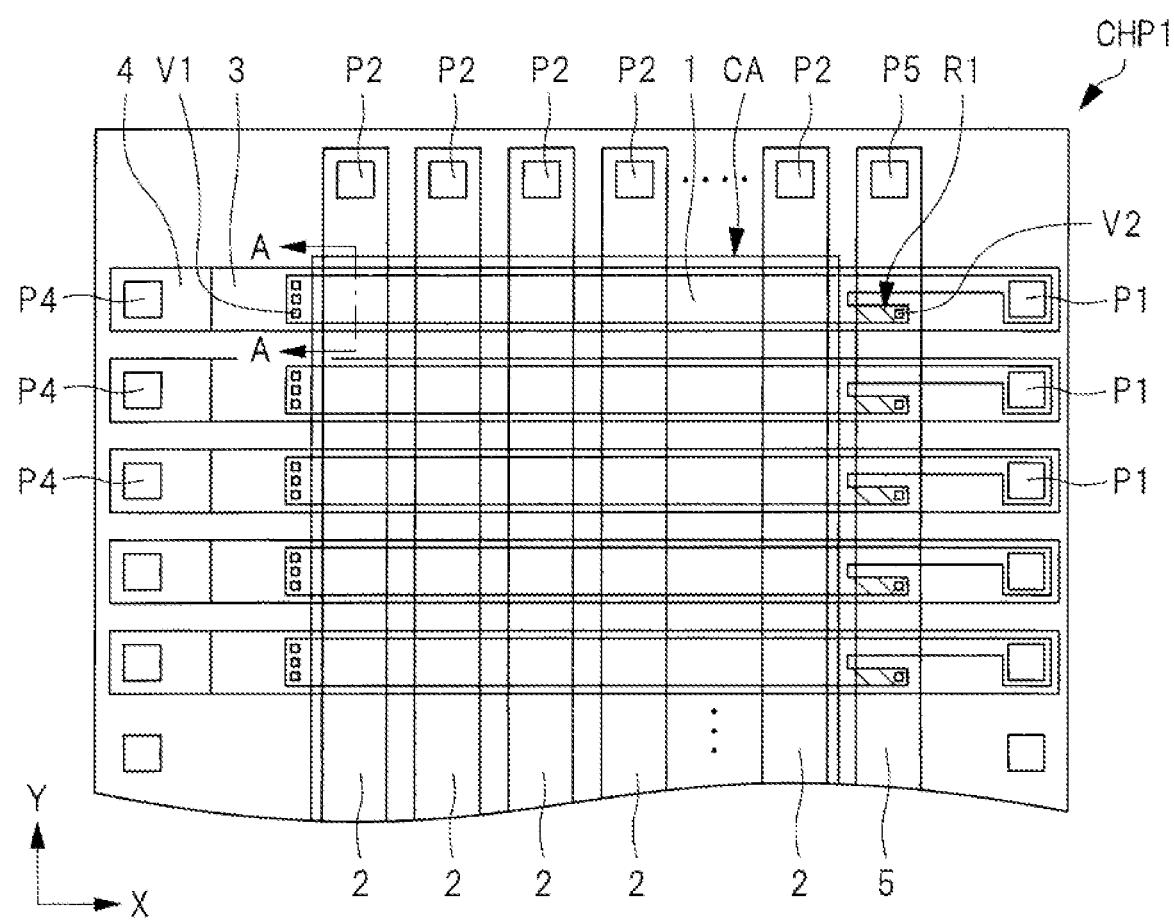
FIG. 2 is a plan view illustrating main parts of the ultrasonic transducer array which is the first embodiment of the invention.
Figure 3:
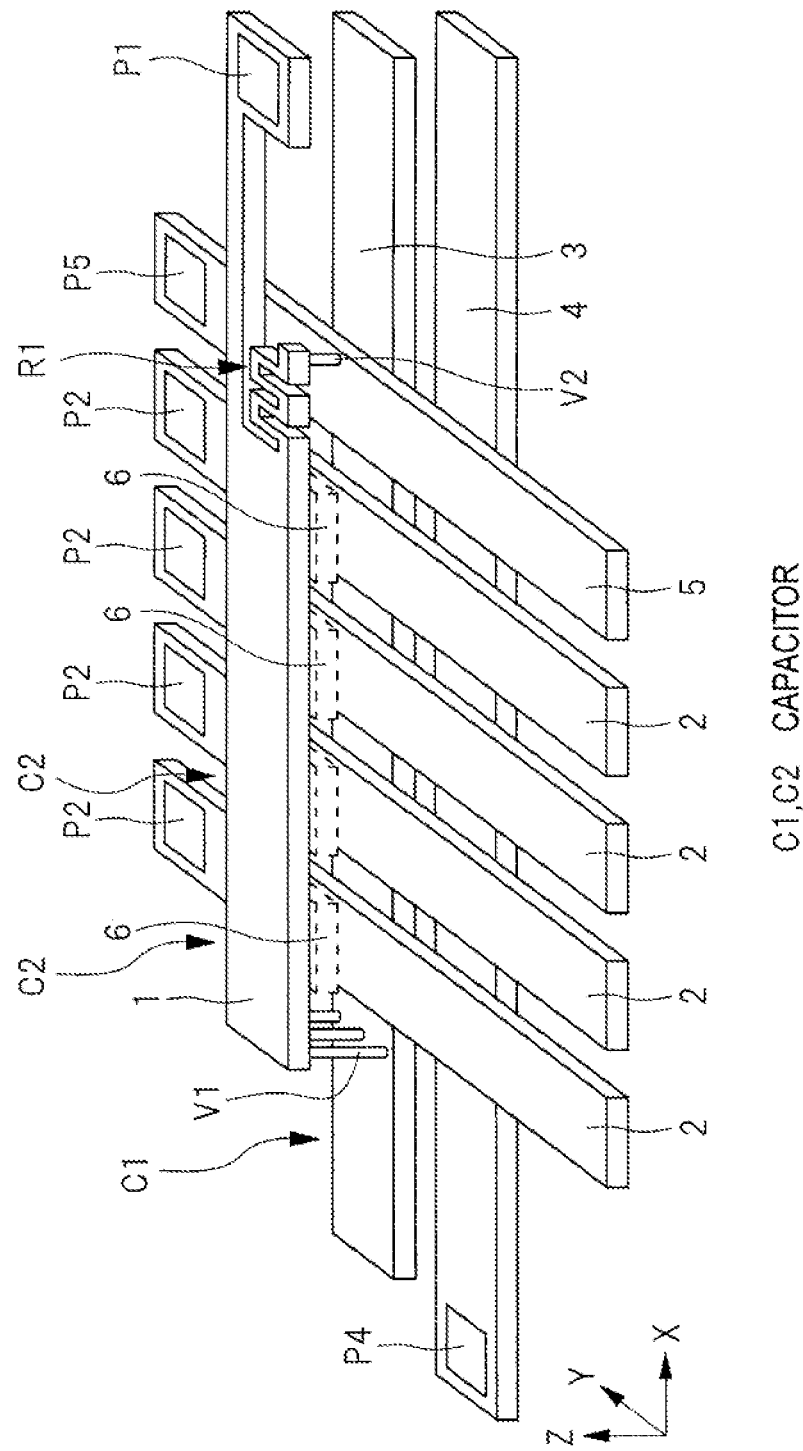
FIG. 3 is a perspective view illustrating the ultrasonic transducer array which is the first embodiment of the invention.
Figure 4:
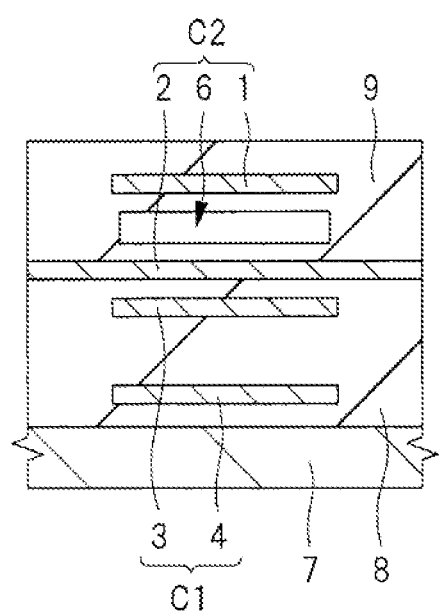
FIG. 4 is a sectional view taken along line A-A of FIG. 2.
Figure 5:
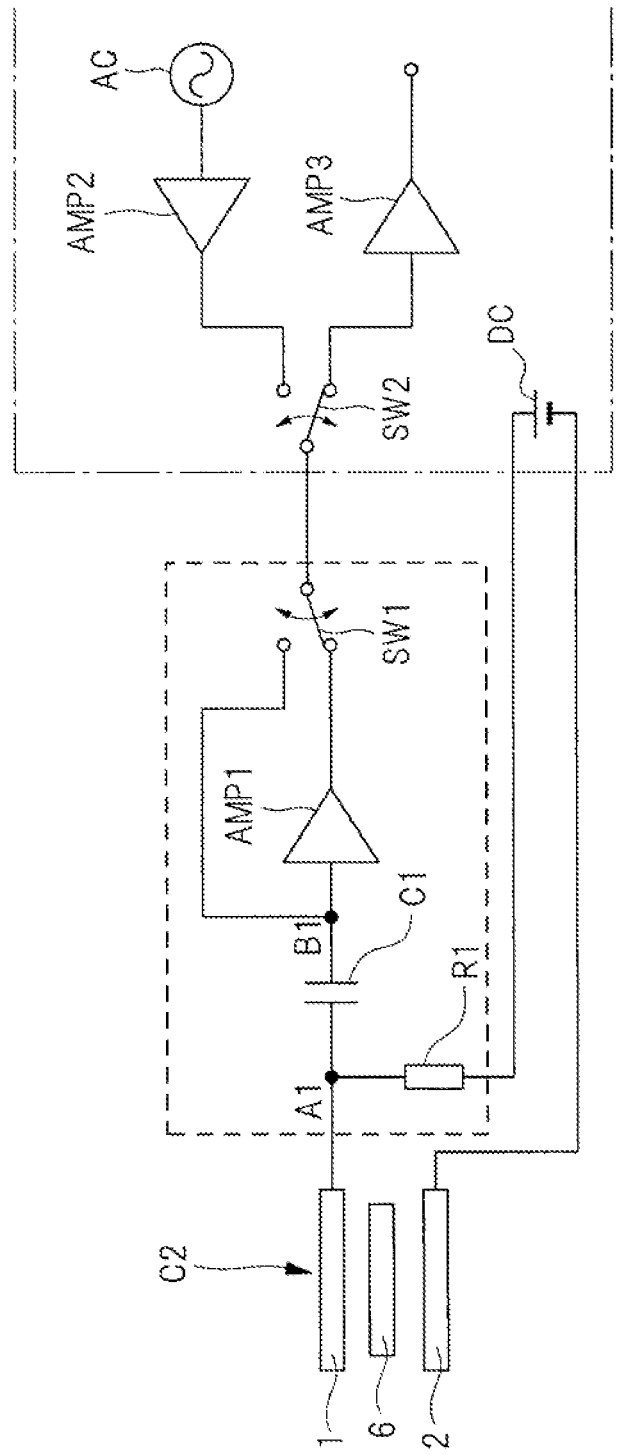
FIG. 5 is a schematic view for explaining a circuit of the ultrasonic transducer array which is the first embodiment of the invention.

Hereinafter, the structure of the ultrasonic transducer array of this embodiment will be described by using FIGS. 1 to 5. FIGS. 1 and 2 are plan views illustrating a chip which is the ultrasonic transducer array of this embodiment. FIG. 2 illustrates the main parts of FIG. 1 in an enlarged manner. FIG. 3 is a perspective view illustrating the wiring structure of the chip which is the ultrasonic transducer array of this embodiment. FIG. 4 is a sectional view taken illustrating the chip which is the ultrasonic transducer array of this embodiment. FIG. 4 is a sectional view taken along line A-A of FIG. 2. FIG. 5 is a schematic view for explaining the circuit of the ultrasonic transducer array of this embodiment.

The ultrasonic transducer array in this application indicates not only a simple cell array (a cell array CA to be described later) in which a plurality of cells of electrostatic capacitance ultrasonic transducers are arranged, but also an array which includes a cell array and a wiring, a via, and an element (for example, an electrostatic capacitance element and a resistance element) which are connected to the cell array. In other words, the ultrasonic transducer array is a concept close to one chip. However, since the ultrasonic transducer array is not a concept larger than one chip, the cell array, the wiring, the via, and the element configuring the ultrasonic transducer array are formed in one chip.

FIG. 1 is a plan view illustrating the entire chip CHP1 on which the electrostatic capacitance ultrasonic transducer of this embodiment is formed. The chip CHP1 has a principal surface (an upper surface, a surface) and a back surface (lower surface) which are positioned to opposite to each other in a thickness direction. FIG. 1 illustrates a plan view (top view) on the principal surface side of the chip CHP1.

As illustrated in FIG. 1, the planar shape of the chip CHP1 is an oblong shape, that is, a rectangle shape, for example. Herein, the chip CHP1 extends in a Y direction. In other words, the longitudinal direction of the chip CHP1 is a Y direction, and the lateral direction of the chip CHP1 is an X direction. The X direction and the Y direction are directions along the principal surface of the chip CHP1 and the principal surface of the semiconductor substrate (to be described later) and are orthogonal to each other in plan view. In the principal surface of the chip CHP1, the cell array (cell area) CA and a plurality of bonding pads (hereinafter, referred to as pads) PD which are positioned in a central portion in plan view are arranged. For example, the planar shape of the cell array CA is an oblong shape, that is, a rectangle shape. The area surrounding the cell array CA in plan view is a peripheral area which does not overlap with the cell array CA in plan view, and the pad PD is formed in the peripheral area.

A plurality of pads PD are arranged to be adjacent to the cell array CA in plan view and positioned between the cell array CA and the end portion of the chip CHP1. The plurality of pads PD adjacent to the cell array CA in the X direction are arranged side by side in the Y direction. The plurality of pads PD adjacent to the cell array CA in the Y direction are arranged side by side in the X direction. The pad PD is a terminal for input/output of the chip CHP1, and a bonding wire or the like is electrically connected to the pad PD.

As illustrated by a dashed line in FIG. 1, a channel CH extending in the X direction is formed in the cell array CA. A plurality of channels CH are arranged side by side in a longitudinal direction (Y direction) of the cell array CA, and the plurality of pads PD are formed side by side as many as the channels CH in the Y direction in the area adjacent to the cell array CA in the X direction. For example, the number of the channels CH aligned in the Y direction is about 100 to 200. However, in order to make the drawing easy to understand, FIG. 1 illustrates only one area which is surrounded by the dashed line representing the range of the channel CH. Each of the channels CH has one to several hundred cells. Therefore, for example, 100 to 100,000 cells are arranged in a matrix shape in the entire cell array CA.

FIG. 2 illustrates a plan view of the longitudinal end portion of the chip CHP1, and FIG. 3 illustrates the structure illustrated in FIG. 2 in a bird's eye view. FIGS. 2 and 3 do not illustrate an interlayer insulating film which covers each of the cell array CA, the electrode, and the like. In addition, FIG. 2 transparently illustrates each of the electrodes overlapped with each other in a vertical direction. In addition, in FIG. 2, a hatching is applied only to a resistance element R1.

As illustrated in FIGS. 2 and 3, in the cell array CA, a plurality of lower electrodes 2 which extend in the Y direction and are made of conductive films arranged in the X direction. Each of the plurality of lower electrodes 2 extends to the outside of the cell array CA in plan view. Each of all the lower electrodes 2 is partially overlapped with the cell array CA in plan view. The pad P2 is formed in the upper surface of the end portion of the lower electrode 2 in the Y direction. The plurality of pads P2 correspond to the plurality of pads PD aligned in the X direction in FIG. 1.

A DC bias wiring (DC power supply wiring) 5 extending in the Y direction is formed near the lower electrode 2 which is endmost in the X direction among the plurality of aligned lower electrodes 2. A pad P5 is formed on the upper surface of the end portion of the DC bias wiring 5 in the Y direction. The pad P5 corresponds to one of the pads PD aligned in the X direction in FIG. 1. All of the DC bias wiring 5 and the plurality of lower electrodes 2 are formed to have the same height. The entire DC bias wiring 5 is not overlapped with the cell array CA in plan view. In other words, in plan view, the DC bias wiring 5 is separated from the cell array CA and the cell (vibrator) formed in the cell array CA.

In the cell array CA, an upper electrode 1 is formed with a gap (cavity part) 6 above the lower electrode 2. The upper electrode 1 is a conductive film extending in the X direction, and a plurality of upper electrodes are arranged side by side in the Y direction. A pad P1 is formed on the upper surface of a lead-out wiring which extend in the X direction from one end portion of each of the plurality of upper electrodes 1 in the X direction. The plurality of pads P1 correspond to the plurality of pads PD which are aligned in the Y direction along one side extending in the Y direction among four sides of the cell array CA of FIG. 1. However, in order to make the drawing easy to understand, FIG. 3 illustrates only one upper electrode 1. In other words, only the upper electrode 1 of one channel CH among the plurality of channels CH (see FIG. 1) formed in the Y direction is illustrated. Practically, the upper electrode 1 extending in the X direction in plan view is formed from each of the plurality of pads P1 aligned in the Y direction. In addition, in FIG. 2, the upper electrode 1, an upper electrode 3, a lower electrode 4, the resistance element R1, and vias V1 and V2 in some channels is not illustrated.

Each of all the upper electrodes 1 is partially overlapped with the cell array CA in plan view. In the cell array CA, the upper electrode 1 and the lower electrode 2 are orthogonal to each other in plan view. One gap 6 between the upper electrode 1 and the lower electrode 2 is formed in the place where one upper electrode 1 and one lower electrode 2 are overlapped with each other in plan view. In other words, the gap 6 has a layout which is rectangle in plan view.

The lower electrode 2, the gap 6, and the upper electrode 1 which are overlapped with each other in plan view configure one cell of the electrostatic capacitance ultrasonic transducer (CMUT: Capacitive Micro-machined Ultrasonic Transducer). The CMUT is an electrostatic capacitance element (capacitor) which can be vibrated acoustically. In other words, the upper electrode 1 and the lower electrode 2 are coupled capacitively through the gap 6, and the layer including the upper electrode 1 on the gap 6 configures a membrane (flexible film) which is a movable part. By applying a voltage to the capacitor C2 configured by the lower electrode 2, the gap 6, and the upper electrode 1, an electrostatic force is generated between the upper electrode 1 and the lower electrode 2. If an AC voltage is applied as a voltage at this time, the electrostatic force is changed periodically, and the membrane is vibrated so as to oscillate ultrasonic waves. Conversely, when the capacitor C2 receives ultrasonic waves, the membrane is vibrated to generate an electrical signal. In other words, the capacitor C2 is an element which is capable of transmitting and receiving ultrasonic waves. The cell of the CMUT is a minimum unit of vibrator (ultrasonic wave vibrator) which is capable of generating ultrasonic waves to transmit ultrasonic waves and receive ultrasonic waves. The vibrator is configured by an electrostatic variable capacitance (variable capacitance sensor). The upper electrode 1 and the lower electrode 2 are insulated from each other through the gap 6 and an insulation film (not illustrated).

The "capacitor which vibrates acoustically" in this application is a capacitor which can oscillate sound waves when a voltage is applied, and receive sound waves to vibrate the membrane and generate electrical signals. Conversely, "a capacitor which does not vibrate acoustically" in this application is a capacitor which does not oscillate sound waves even when a voltage is applied, does not include a portion being vibrated when sound waves are received, and does not generate electrical signals even when sound waves are received.

In the cell array CA which is an area where the plurality of lower electrodes 2 extending in the Y direction and the plurality of upper electrodes 1 extending the X direction are orthogonal to each other, the cells of the CMUT are arranged side by side in the matrix shape in plan view. In other words, the cell array CA is an area where the cells which are the capacitors C2 capable of being vibrated acoustically are arranged in matrix. Similarly to the cells, the plurality of gaps 6 are also arranged in a matrix shape in plan view. However, in order to make the drawing easy to understand, FIG. 3 illustrates only one row of gaps 6 aligned in the X direction. Incidentally, the gap 6 is not formed just above the DC bias wiring 5.

The upper electrode 3 which extends in the cell array CA and outside the cell array CA in the X direction in plan view is formed just under the upper electrode 1 and below the lower electrode 2. In addition, the lower electrode 4 which extends in the cell array CA and outside the cell array CA in the X direction in plan view is formed just under the upper electrode 3. In other words, the upper electrode 3 and the lower electrode 4 are overlapped with each other in plan view and are insulated from each other through an insulation film (not illustrated). The upper electrode 3 and the lower electrode 4 coupled capacitively configure an electrostatic capacitance element (capacitor). However, the capacitor C1 configured by the upper electrode 3 and the lower electrode 4 is a capacitor which is not vibrated acoustically. In other words, the ultrasonic waves are not oscillated even when a voltage is applied to the capacitor C1, and even when the capacitor C1 receives ultrasonic waves, the upper electrode 3 and the lower electrode 4 are not vibrated, and electrical signals are not generated.

The upper electrode 3 and the lower electrode 4 face each other in the Z direction (vertical direction) in the area where the electrodes are not overlapped with the cell array CA in plan view as well as in the area where the electrodes are overlapped with the cell array CA in plan view. The Z direction is a direction orthogonal to the X direction and the Y direction and is a direction perpendicular to the principal surface of the chip CHP1 (see FIG. 1) and the principal surface of the semiconductor substrate (to be described later). In addition, the upper electrode 3 and the lower electrode 4 face each other in the Z direction also just under the pad P1. Since the upper electrode 3 and the lower electrode 4 face each other in a wide area as well as in the cell array CA as described above, the capacitor C1 has a high electrostatic capacitance.

The pad P4 is formed on the upper surface of one end portion of the lower electrode 4 in the X direction. The plurality of pads P4 correspond to the plurality of pads PD aligned in the Y direction along one side extending in the Y direction among four sides of the cell array CA in FIG. 1. In addition, although not illustrated, the pad may be formed on the upper surface of one end portion of the upper electrode 3 in the X direction.

The upper electrode 1 and the upper electrode 3 are connected electrically by the through-hole via (hereinafter, simply referred to as a via) V1 which connects the lower surface of the upper electrode and the upper surface of the upper electrode 3, for example. The via V1 is a conductive connection part penetrating the interlayer insulating film (not illustrated).

The upper electrode 1 is electrically connected with the resistance element R1. Herein, as illustrated in FIG. 3, the resistance element R1 is integrated with the conductive film configuring the upper electrode 1 and is configured to have a width narrower than that of the upper electrode 1 in plan view and to have a pattern of meandering in a zigzag shape. In other words, the resistance element R1 has a zigzag layout, has a relatively thin and long conductive path, and has a cross-sectional area smaller than that of the upper electrode 1. Thus, the resistance element has a relatively high resistance value. Incidentally, in FIG. 2, such a meandering pattern of the resistance element R1 is not illustrated, and the resistance element R1 is illustrated in a simplified manner.

Among the end portions of the resistance element R1, the end portion on opposite side to the end portion connected with the upper electrode 1 is electrically connected with the DC bias wiring 5 by the via V2 which connects the lower surface of the resistance element R1 and the upper surface of the DC bias wiring 5, for example. In other words, the upper electrodes 1 of all the channels aligned in the Y direction are connected electrically with the common DC bias wiring 5 through the resistance elements R1 of the channels, respectively. The via V2 is a conductive connection part penetrating the interlayer insulating film (not illustrated).

Each of the pads P1, P2, P4, and P5 includes a metal surface exposed from the interlayer insulating film (not illustrated) and is arranged in a position separated from the cell array CA in plan view. Each of the upper electrodes 1 and 3, the lower electrodes 2 and 4, and the DC bias wiring 5 is a conductive film made of Al (aluminum) or the like. The upper electrode 1 may be made of Si (silicon) film or the like. In addition, each of the upper electrodes 1 and 3, the lower electrodes 2 and 4, and the DC bias wiring 5 has a layout which has a rectangle shape in plan view.

Incidentally, the resistance element R1 is not a part of the upper electrode 1. In addition, a thin pattern which is aligned with the resistance element R1 in the Y direction and is connected with the pad P1 is not a part of the upper electrode 1 and is a lead-out wiring (conductive connection part) for electrically connecting the upper electrode 1 and the pad P1. Therefore, the upper electrode 1 has a layout which has a rectangle shape in plan view. At least the planar shape of the upper electrode 1 which is overlapped with the lower electrode 2 in plan view and configures the capacitor C2 is a rectangle shape.

Next, the cross-sectional structure of each channel will be described by using FIG. 4. As illustrated in FIG. 4, the chip of this embodiment has a substrate 7. The substrate 7 is made of a semiconductor such as single crystal Si (silicon) or SiC (silicon carbide). However, the substrate may be made by using an insulator such as quartz or polyimide depending on application. An interlayer insulating film 8 made of a silicon oxide film, a silicon nitride film, or the like is formed on the substrate 7. The lower electrode 4 and the upper electrode 3 formed in order above the substrate 7 are formed in the interlayer insulating film 8. The periphery of each of the lower electrode 4 and the upper electrode 3 is covered with the interlayer insulating film 8 and is separated from each other through the interlayer insulating film 8.

The lower electrode 2 is formed on the interlayer insulating film 8. In addition, an interlayer insulating film 9 made of a silicon oxide film or the like is formed on the lower electrode 2. The gap 6 and the upper electrode 1 formed in order above the lower electrode 2 are formed in the interlayer insulating film 9. The periphery of each of the gap 6 and the upper electrode 1 is covered with the interlayer insulating film 9. In other words, the gap 6 is a cavity part formed in the interlayer insulating film 9, and the inside of the gap 6 is in a vacuum state, for example. In each channel, the upper electrodes 1 and 3, the lower electrodes 2 and 4, and the gap 6 are overlapped with each other in plan view. That is, the capacitor C1 configured by the upper electrode 3 and the lower electrode 4 and the capacitor C2 configured by the upper electrode 1 and the lower electrode 2 are overlapped with each other in plan view. Herein, each of the interlayer insulating films 8 and 9 is illustrated as one film. However, practically, each of the interlayer insulating films 8 and 9 may be configured by a laminated body of plural insulation films.

Next, the configuration and the operation of the ultrasonic transducer array of this embodiment will be described by using FIG. 5.

The chip CHP1 (see FIG. 1) which is the ultrasonic transducer array of this embodiment is a device which has a plurality of cells as a CMUT (electrostatic capacitance ultrasonic transducer), that is, a plurality of vibrators.

The cell corresponds to the capacitor C2 configured by the upper electrode 1 and the lower electrode 2 illustrated in FIG. 5. Each of the plurality of lower electrodes 2 is connected with the negative side terminal of the DC power source (DC voltage source) DC, and the positive side terminal of the DC power source DC is connected with the upper electrode 1 through the resistance element R1. In addition, the positive side terminal of the DC power source DC is connected to a first terminal of the capacitor C1 through the resistance element R1, and the upper electrode 1 is also connected to the first terminal of the capacitor C1. A second terminal of the capacitor C1 is connected to the main body side of an ultrasonic echo diagnostic device (an ultrasound diagnostic apparatus, an ultrasonic image apparatus) or the like through an amplifying circuit AMP1. The ultrasonic echo diagnostic device will be described later by using FIG. 10. The amplifying circuit AMP1 serves to amplify the signal which is received from the plurality of vibrators of the CMUT and to transmit the signal to the main body side of the ultrasonic echo diagnostic device. In FIG. 5, the configuration of the main body of the ultrasonic echo diagnostic device is illustrated to be surrounded by a one-dot chain line.

The first terminal of the capacitor C1 corresponds to the upper electrode 3 illustrated in FIGS. 2 and 3, for example. In this case, the second terminal of the capacitor C1 corresponds to the lower electrode 4 illustrated in FIGS. 2 and 3. Conversely, the first terminal may correspond to the lower electrode 4, and the second terminal may correspond to the upper electrode 3. Hereinafter, the description will be given about a case where the first terminal corresponds to the upper electrode 3, and the second terminal corresponds to the lower electrode 4.

The resistance element R1 illustrated in FIG. 5 corresponds to the resistance element R1 illustrated in FIGS. 2 and 3. The DC bias wiring 5 illustrated in FIGS. 2 and 3 is connected to the positive side terminal of the DC power source DC. In other words, a DC bias voltage is supplied from the DC bias wiring 5 to the resistance element R1 of each channel through the via V2 illustrated in FIG. 3. As illustrated in FIG. 5, the resistance element R1, the first terminal (upper electrode 3) of the capacitor C1, and the upper electrode 1 are connected to a node A1. In addition, the second terminal (lower electrode 4) of the capacitor C1 and the amplifying circuit AMP1 are connected to the node B1.

Herein, an AC power source AC is connected to the node B1 through the amplifying circuit AMP2. Practically, transmission/reception switching switches SW1 and SW2 which are switching elements which are turned on during the transmission operation by the CMUT and are turned off during the reception operation by the CMUT are connected between the AC power source AC and the node A1. The transmission/reception switching switches SW1 and SW2 are conducted at the time of applying a driving voltage from the amplifying circuit AMP2, so as to apply the driving voltage to the capacitor C2 through the capacitor C1. Simultaneously, the amplifiers AMP1 and AMP3 are separated to prevent that the amplifiers AMP1 and AMP3 are broken when the driving voltage is applied. A diode, a FET (Field Effect Transistor), or the like can be used as a circuit element which serves as the transmission/reception switching switches SW1 and SW2.

The capacitor C1 serves to prevent that the amplifying circuit AMP1 is broken due to the voltage supplied from the DC power source DC. Incidentally, simultaneously, the capacitor C1 serves to prevent that the amplifying circuit AMP2 is broken when a voltage is supplied from the DC power source DC to the output terminal of the amplifying circuit AMP2. However, in a case where the amplifying circuit AMP2 can be protected without the capacitor C1, the AC power source AC may be connected to the node A1 through the amplifying circuit AMP2. The AC power source AC is a driving signal source for driving the CMUT during the transmission operation of the CMUT.

In the operation (transmission operation) of generating ultrasonic waves by using the CMUT, when the DC and AC voltages are superimposed and applied to the lower electrode 2 and the upper electrode 1, an electrostatic force acts between the lower electrode 2 and the upper electrode 1, and the membrane on the gap 6 (see FIG. 3) of each vibrator is vibrated in a vertical direction at the frequency corresponding to the operation frequency of the AC power source AC due to the balance with the force of a spring of the membrane. At this time, a maximum potential difference between the upper electrode 1 and the lower electrode 2 is 300 V, for example. Accordingly, ultrasonic waves (ultrasonic pulse) of several MHz (for example, 1 to 10 MHz) are generated from the vibrator.

The DC voltage is applied from the DC power source DC illustrated in FIG. 5 to the capacitor C2. In addition, the AC voltage is applied from the AC power source AC illustrated in FIG. 5 to the capacitor C2. The voltage of the AC power source AC is 10 to 100 V or 100 V or more, for example. The voltage of the DC power source DC is 100 to 200 V, for example. The electrostatic capacitance of the capacitor C1 is about 1000 pF, for example. The resistance value of the resistance element R1 is about 500 kΩ, for example.

In the reception operation of the CMUT, the membrane is vibrated by the pressure of the ultrasonic waves reaching the membrane of each vibrator, and the ultrasonic waves can be detected by the change of the electrostatic capacitance between the lower electrode 2 and the upper electrode 1. That is, the displacement of the interval between the lower electrode 2 and the upper electrode 1 due to reflected waves is detected as the change of the electrostatic capacitance (the electrostatic capacitance of each vibrator). In this way, the electrostatic capacitance ultrasonic transducer is used to transmit and receive the ultrasonic waves, so that a tomographic image of a living tissue can be imaged, for example. That is, the CMUT is a capacity detection type ultrasonic sensor. When the CMUT is used to operate transmitting and receiving in this way, in the capacitor C1 which is not vibrated acoustically, a part of the capacitor C1 is not vibrated, and the ultrasonic waves are not transmitted and received.

The capacitor C1 is a DC block capacitor which is inserted between the DC power source DC and the amplifying circuit AMP1 to prevent that the amplifying circuit AMP1 is broken by the voltage supplied from the DC power source DC. Since the capacitor C1 is formed, only a minute AC signal flows in the amplifying circuit AMP1. One of the reasons why the resistance element R1 is connected to the positive terminal of the DC power source DC is to convert the received ultrasonic waves into the voltage when the voltage is changed in the node A1 by the current which flows from the DC power source DC due to the electrostatic capacitance change of the capacitor C2 caused by the vibration of the membrane. Another one of the reasons why the resistance element R1 is connected to the positive terminal of the DC power source DC is to prevent that a large current flows from the DC power source DC to an inspection target (for example, a living body) when electric leakage occurs due to a defect of an ultrasonic probe (see FIG. 10) including the chip mounted with the CMUT. In addition, still another one of the reasons why the resistance element R1 is connected to the positive terminal of the DC power source DC is to prevent that a large sudden current flows in the amplifying circuit AMP1 when the ultrasonic transducer array is powered on. In addition, still another one of the reasons why the resistance element R1 is connected to the positive terminal of the DC power source DC is to prevent that the received signals interfere between the cells of different channels adjacent to each other in the Y direction (see FIG. 2). In other words, the resistance element R1 is formed so as to weaken the electrical coupling between the channels.

Because of the above reasons, the capacitor C2, the resistance element R1, and the amplifying circuit AMP1 are required for each of the plurality of channels configuring the cell array CA (see FIG. 2) of the CMUT. In other words, a plurality of the elements and the circuits in the range surrounded by the dashed line in FIG. 5 are required as many as the channels. One of the main features of this embodiment is that the capacitor C1 which is not vibrated acoustically differently from the capacitor C2 which is the vibrator configuring the CMUT is mounted together with the capacitor C2 in the chip. In addition, one of the main features of this embodiment is that the resistance element R1 is mounted together with the capacitor C2 in the chip. As illustrated in FIG. 2, the resistance element R1 and the DC bias wiring 5 are arranged outside the cell array CA in plan view. In addition, as illustrated in FIGS. 2 and 3, the capacitor C1 arranged just under the capacitor C2 is partially arranged outside the cell array CA in plan view.

<Effect of Ultrasonic Transducer Array of This Embodiment>

Figure 12:
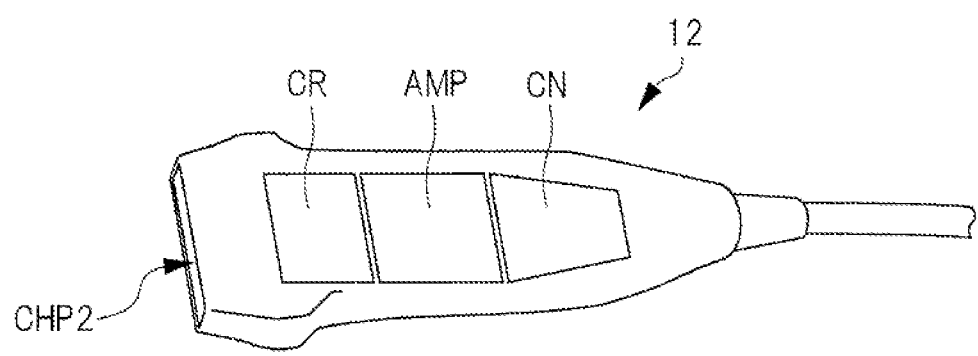
FIG. 12 is a schematic view illustrating an ultrasonic probe mounted with an ultrasonic transducer array as a comparative example.

Hereinafter, the effect of the ultrasonic transducer array of this embodiment is described by using FIG. 12. FIG. 12 is a schematic view of the ultrasonic probe in which an ultrasonic transducer array as a comparative example is mounted.

As described above, it is necessary to connect the resistance element and the DC block capacitor to the channel including a plurality of cells configuring the CMUT. Herein, for example, about 100 to 200 channels are arranged side by side in one chip. Thus, about 100 to 200 of the resistance elements and the DC block capacitors which are connected to the respective channels are needed.

In FIG. 12, the probe which has the chip CHP2 including the CMUT at the tip, that is, an ultrasonic probe 12 is illustrated as a comparative example. A plurality of printed substrates are mounted in the ultrasonic probe 12 of the comparative example. For example, the plurality of printed substrates in the ultrasonic probe 12 includes a substrate CR in which a plurality of the resistance elements and a plurality of the DC block capacitors are mounted as many as the channels, a substrate AMP in which the amplifying circuit AMP1 illustrated in FIG. 5 is mounted, and a substrate CN in which a connector circuit which connects the amplifying circuit AMP1 and the ultrasonic echo diagnostic device is mounted.

Those substrates CR, AMP, and CN may be printed substrates different from each other or may be one printed substrate. However, in the comparative example, the plurality of resistance elements as a passive component and the plurality of block capacitors as a passive component are mounted as many as the channels of the CMUT in the printed substrate. Thus, when all the passive components and the chips of the substrates CR, AMP and CN are mounted in one printed substrate, the area of the printed substrate becomes considerably large. Accordingly, although the substrates CR, AMP and CN are arranged side by side in FIG. 12, practically, the plurality of printed substrates are arranged to be overlapped with each other in the ultrasonic probe 12. For example, 30 to 40% of the mounting area of all the printed substrates in the ultrasonic probe 12 is closed by the area in which the resistance element and the block capacitor are mounted.

Herein, the resistance elements as a passive component and the block capacitors as a passive component are contained as many as the channels in the ultrasonic probe 12. Thus, the ultrasonic probe 12 is enlarged to cause the following problems. That is, for example, there occur a problem that a grip of the ultrasonic probe 12 is hard to grasp and a problem that it is difficult to make the ultrasonic probe 12 be brought into contact with an object (living body) at a desired angle.

In this regard, in this embodiment, as illustrated in FIGS. 2 and 3, the resistance elements R1 and the capacitors C1 as the DC block capacitor are mounted together in the chip CHP1 in which the cells of the CMUT are mounted. Accordingly, it is not necessary to prepare the resistance element as a passive component and the DC block capacitor as a passive component. Thus, the ultrasonic transducer array can be miniaturized. That is, the performance of the ultrasonic transducer array can be improved.

The resistance element R1 can be formed by changing the layout of the conductive film configuring the upper electrode 1, for example. Although the capacitor C1 is different from the capacitor C2 in that the capacitor C1 does not have the membrane and is not vibrated acoustically, the capacitor C1 can be formed in the chip CHP1 by using the technology similar to the capacitor C2. That is, there is no particular difficulty when the resistance element R1 and the capacitor C1 are mounted in the chip CHP1. The resistance element R1 and the capacitor C1 can be formed by using the existing technology. In addition, the resistance element R1 can be formed to be added in the periphery of the cell array CA in plan view, and the capacitor C1 can be formed in the area of being overlapped with the cell array CA in plan view and the area of the periphery of the cell array CA. Thus, although the resistance element R1 and the capacitor C1 can be formed in the chip CHP1, the enlargement of the area of the chip CHP1 can be prevented. That is, in the chip CHP1 illustrated in FIG. 1, pads for wiring connection by wire bonding or flip-chip bonding are provided on the both sides of the cell array CA.

For example, the cell array CA has a width of 4 mm. However, it is necessary to prevent such problems that the cell array CA is broken due to the contact with the bonding device during the wiring connection, or the cell array CA is covered with a member for wiring connection to hinder acoustic propagation. In order to prevent those problems, the bonding pad PD is necessarily provided to be sufficiently separated from the cell array CA. As a result, for example, the chip CHP1 has a width of 8 mm in the lateral direction. In this embodiment, the capacitor C1 and the resistance element R1 can be formed by using the areas of 2 mm on both sides of the cell array CA. Thus, the chip area can be effectively utilized.

Herein, the DC bias wiring 5 is formed to be adjacent to the cell array CA in plan view in parallel with the lower electrode 2 of the cell array CA, and the upper electrodes 1 of the channels are connected through the respective resistance elements R1 of the channels to the DC bias wiring 5 in parallel. In order to realize such a connection, the DC bias wiring 5 extends in parallel with the lower electrode 2. In other words, the DC bias wiring 5 extends in a direction in which the channels are aligned. Accordingly, the DC bias voltage can be supplied to the upper electrode 1 of each channel through the resistance element R1 of each channel while preventing the enlargement of the area of the chip CHP1.

Each of the upper electrodes 1 and 3 and the lower electrodes 2 and 4 has a layout which is a rectangle shape in plan view. Accordingly, the electrostatic capacitance of each capacitor C2 which is a vibrator can be increased to improve the sensitivity of the CMUT, and the electrostatic capacitance of the capacitor C1 can be increased. In order that the capacitor C1 serves as a DC block capacitor, it is necessary to have a relatively large electrostatic capacitance (for example, 1000 pF). Thus, in order that the capacitor C1 satisfies a desired electrostatic capacitance characteristic, the area where the upper electrode 3 and the lower electrode 4 face each other is desirably large. For this reason, in this embodiment, the capacitor C2 is not only formed in the area of being overlapped with the cell array CA in plan view but also extends to the area outside the cell array CA. For example, in the peripheral area surrounding the cell array CA in plan view, the upper electrode 3 and the lower electrode 4 configuring the capacitor C2 can be formed to extend to the area just under the pad P1. Accordingly, the enlargement of the area of the chip CHP1 can be prevented, and the electrostatic capacitance of the capacitor C1 can be increased.

Although the capacitor C1 is provided under the capacitor C2, the thickness of the layer including the capacitor C1 and the semiconductor substrate 7 (see FIG. 4) under the capacitor C2 is sufficiently small with respect to the ultrasonic waves transmitted and received in the CMUT. For example, the thickness can be set to one twentieth or less of the wavelength of the ultrasonic waves, and thus a negative effect is not made on the acoustic characteristic of the ultrasonic transducer array. In addition, the capacitor C1 has a thickness similar to that of the capacitor in which ceramics are laminated. As a result, the capacitor C1 is configured not to have a hard structure and to have a thin structure having a total thickness of about several micrometers in which relatively flexible materials such as an aluminum film and a silicon oxide film are laminated. For this reason, it can be prevented that a negative effect is not made on the acoustic characteristic of the ultrasonic transducer array. Specifically, in a case where the chip is configured of a hard material, the acoustic impedance of the chip and the membrane becomes excessively larger than the acoustic impedance of the object (living body), water, or the like. Thus, the ultrasonic waves are reflected between the CMUT and the subject, and as a result, the sensitivity of the ultrasonic transducer array is deteriorated. On the other hand, in this embodiment, the chip is configured of a relatively flexible material. Thus, the deterioration of the sensitivity of the ultrasonic transducer array can be prevented.

Incidentally, herein, the description is given about a case where the resistance element R1 illustrated in FIG. 3 is formed in a layout of meandering thin, and the resistance value of the resistance element R1 is set to be high. The resistance element R1 may be configured of a material (for example, W (tungsten) or Ti (titanium)) which has a resistivity higher than that of the upper electrode 1. In this case, the upper electrode 1 and the resistance element R1 are configured by separate films formed by separate processes. However, the upper electrode 1 and the resistance element R1 may be brought into contact with each other or the upper electrode 1 and the resistance element R1 may be connected electrically through a wiring, a via, and the like.

Herein, the description is given about a case where the upper electrodes 1 and 3 are connected through the via V1. However, without the via V1, the upper electrodes 1 and 3 may be connected electrically through another path. For example, the pad which is exposed from the interlayer insulating film may be formed on the upper surface of the end portion of the upper electrode 3 in the extending direction, and the pad and the pad P1 may be connected electrically through the bonding wire, the printed substrate, and the like.

The upper electrode 1 may be connected electrically not to the upper electrode 3 but to the lower electrode 4.

First Modification

Figure 6:
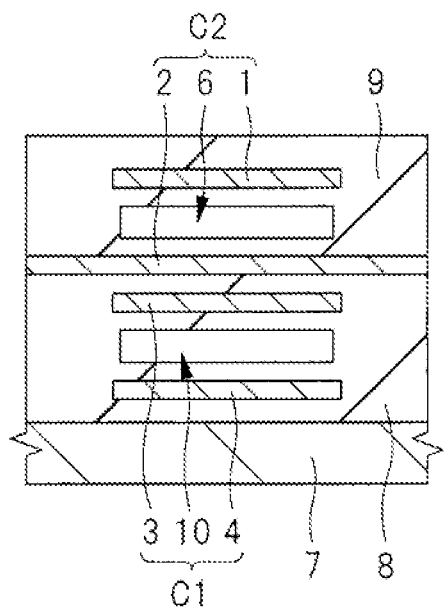
FIG. 6 is a sectional view illustrating an ultrasonic transducer array which is a first modification of the first embodiment of the invention.

As illustrated in FIG. 6, a gap 10 may be formed between the upper electrode 3 and the lower electrode 4 configuring the capacitor C1. FIG. 6 is a sectional view illustrating an ultrasonic transducer array which is a first modification of this embodiment.

The inside of the gap 10 of which the periphery is covered with the interlayer insulating film 8 is in a vacuum state, for example. The upper electrode 3 is arranged just above the gap 10. However, the layer between the gap 10 and the lower electrode 2 can be thicker than the membrane formed above the gap 6, and the layer is not vibrated even when the voltage is applied to the capacitor C1. In addition, a plurality of partition walls or columns may be provided in the gap 10 to suppress the deformation of the layer. That is, the capacitor C1 is an electrostatic capacitance element which is not vibrated acoustically and does not transmit and receive ultrasonic waves.

Second Modification

Figure 7:
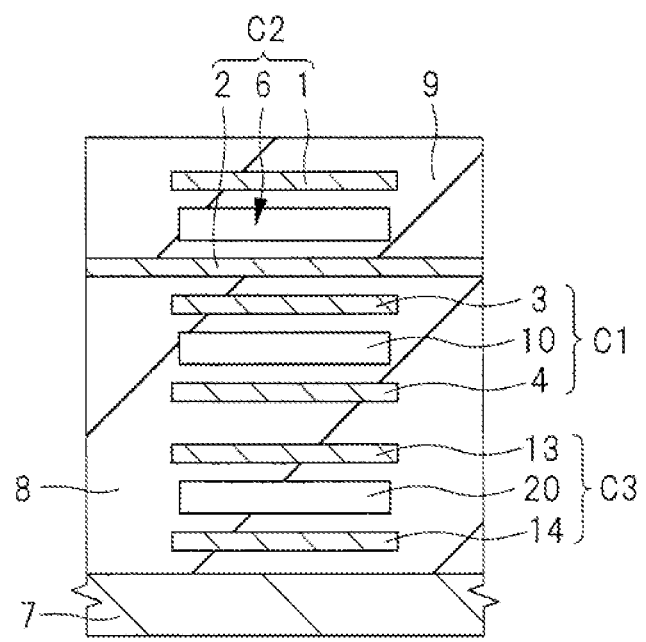
FIG. 7 is a sectional view illustrating an ultrasonic transducer array which is a second modification of the first embodiment of the invention.

As illustrated in FIG. 7, the capacitor C3 which has the same role as the capacitor C1 may be formed just under the capacitor C1. FIG. 7 is a sectional view illustrating an ultrasonic transducer array which is a second modification of this embodiment.

The capacitor C3 has the same structure as the capacitor C1. That is, in the interlayer insulating film 8, the capacitor C3 is configured by a lower electrode 14 and an upper electrode 13 which face each other in the vertical direction. Herein, the gap 10 is formed between the lower electrode 4 and the upper electrode 3, and a gap 20 is formed between the lower electrode 14 and the upper electrode 13 above the lower electrode 14. However, those gaps may not be formed. In other words, for example, only the interlayer insulating film 8 may be formed in each of the space between the lower electrode 4 and the upper electrode 3 and the space between the lower electrode 14 and the upper electrode 13.

The capacitor C1 and the capacitor C3 are connected in parallel with each other. Accordingly, the effective area of the capacitor C1 illustrated in FIG. 5 is increased. Thus, it is possible to increase the electrostatic capacitance of the capacitor C1 illustrated in FIG. 5. That is, even in a case where the capacitor C1 illustrated in FIG. 5 obtains a relatively high electrostatic capacitance characteristic, when a plurality of capacitors are laminated under the capacitor C2, a desired capacitance characteristic can be obtained without increasing the area of the chip.

Third Modification

Figure 8:
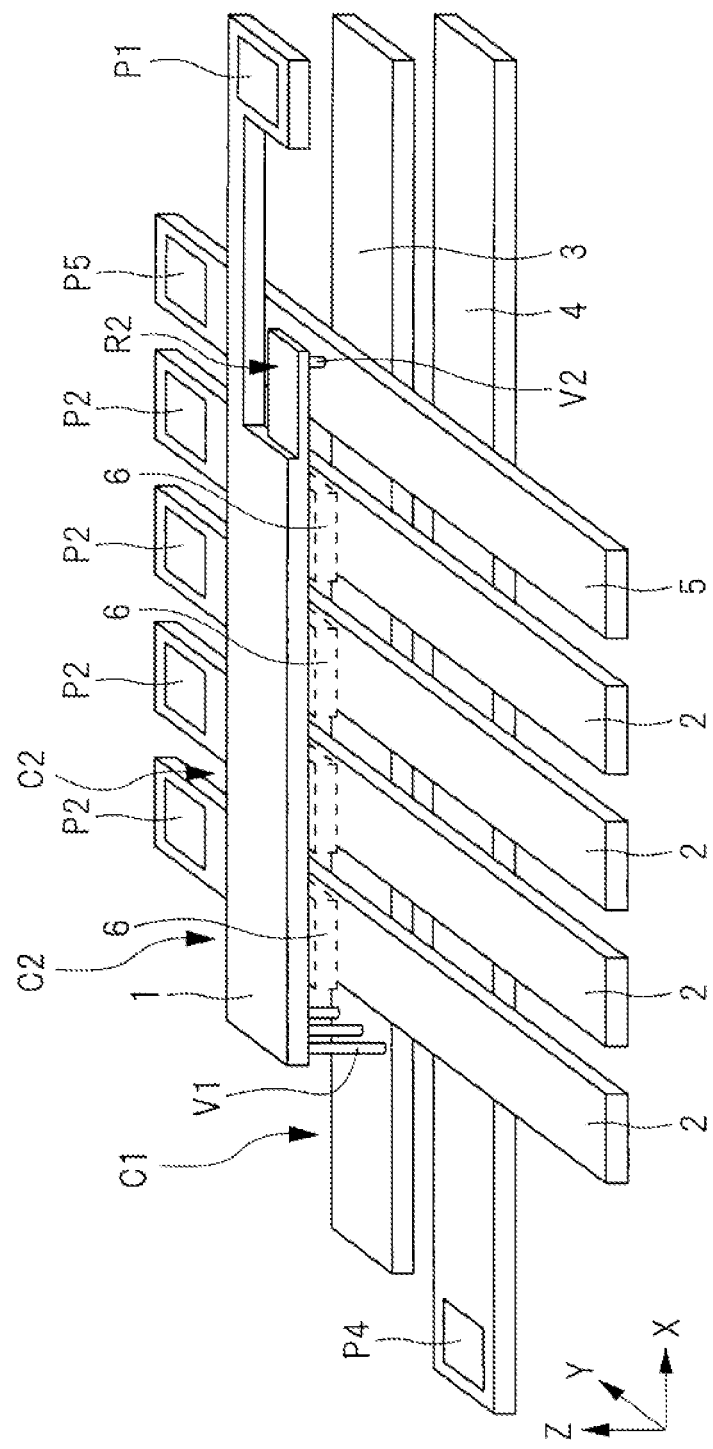
FIG. 8 is a perspective view illustrating an ultrasonic transducer array which is a third modification of the first embodiment of the invention.

As illustrated in FIG. 8, the resistance value of the resistance element R2 may be increased not by forming the resistance element R2 in a thin layout but by thinning a film configuring the resistance element R2. That is, by thinning the film of the resistance element R2, the cross-sectional area becomes small, and the resistance value is increased. FIG. 8 is a perspective view illustrating an ultrasonic transducer array which is a third modification of this embodiment.

In this case, the material of the resistance element R2 may be the same as or different from the upper electrode 1. For example, such a resistance element R2 can be formed by forming the pattern configuring the upper electrode 1 and the resistance element R2, and then etching only the pattern of the portion configuring the resistance element R2.

Fourth Modification

Figure 9:
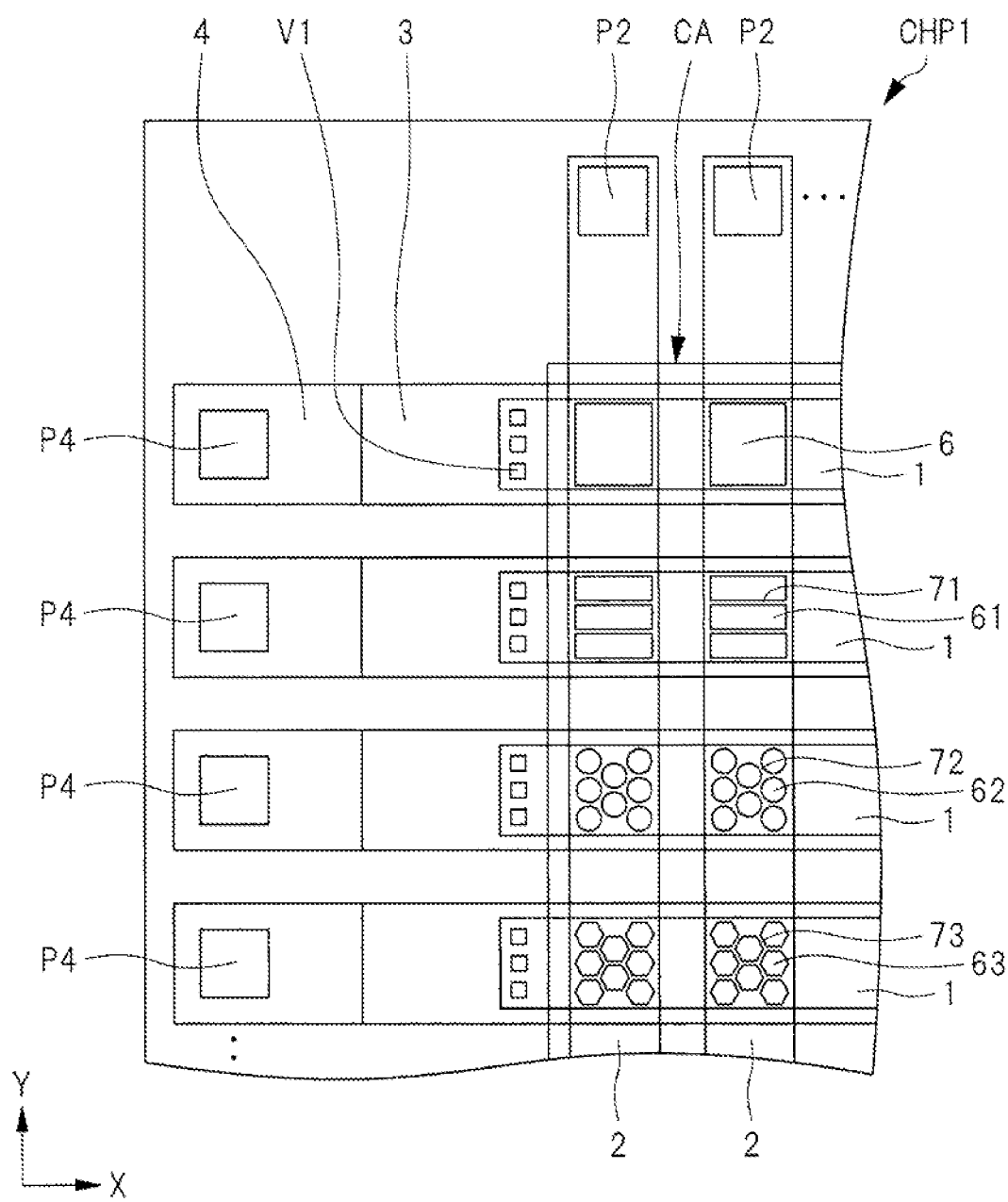
FIG. 9 is a plan view illustrating an ultrasonic transducer array which is a fourth modification of the first embodiment of the invention.

FIG. 9 is a plan view illustrating an ultrasonic transducer array which is a fourth modification of the first embodiment of the invention. FIG. 9 illustrates a plurality of modifications in a case where the gap between the electrodes is divided into a plurality of pieces.

The gap 6 in the cell array CA is formed in the area where the upper electrode 1 and the lower electrode 2 are overlapped with each other in plan view. Desirably, one gap 6 is provided in each area, and the shape is made rectangle for the utilization of the chip area.

Incidentally, when the gap 6 is expanded, the distance between the fulcrums of the membrane is widened, and the membrane may become excessively soft. As a result, the resonance frequency is decreased, and the sensitivity in the high frequency band is deteriorated. In this case, as illustrated in FIG. 9, the partition walls 71, 72, and 73 are formed in the gap 6, and the gap 6 may be divided into a plurality of sub gaps 61, 62, and 63 to increase the resonance frequency of the membrane. At this time, the shape of the sub gap may be a circular shape (see the sub gap 62) or a hexagonal shape (see the sub gap 63) in addition to a rectangle shape (see the sub gap 61). In a case where the sub gaps 61 to 63 are provided, it is desirable in terms of the sensitivity that the sub gaps are arranged to spread as closely as possible in the area occupied by the gap 6.

Second Embodiment

Figure 10:
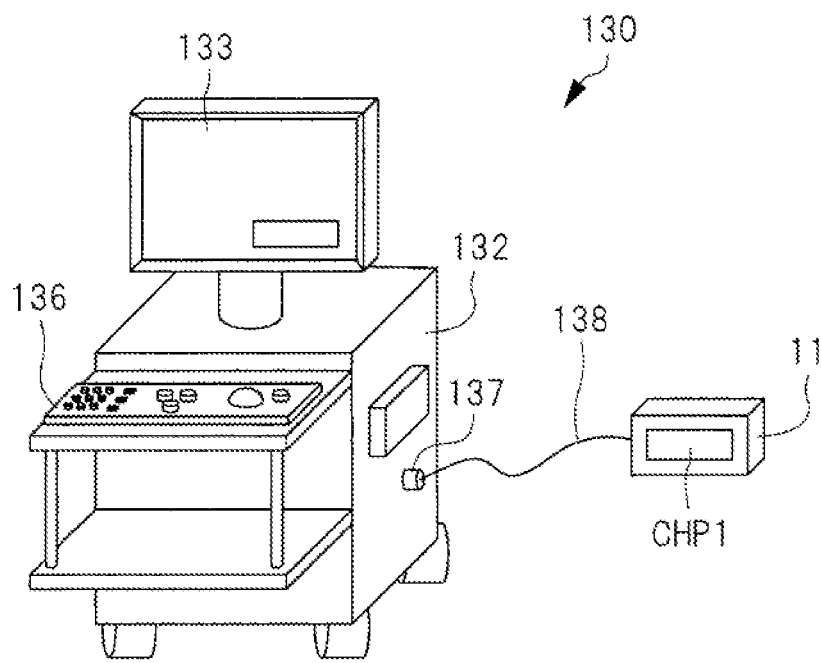
FIG. 10 is a perspective view illustrating an ultrasonic echo diagnostic device including an ultrasonic probe of a second embodiment of the invention.
Figure 11:
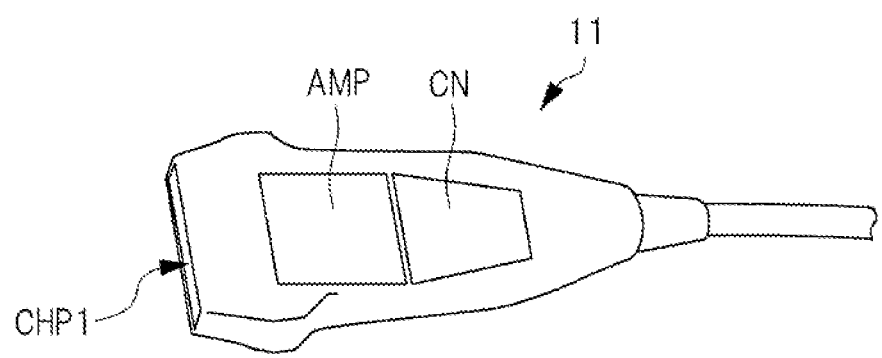
FIG. 11 is a schematic view illustrating the ultrasonic probe of the second embodiment of the invention.

Next, a case where the ultrasonic transducer array (chip) of any one of the first embodiment and the first to fourth modifications of the first embodiment is applied to the ultrasonic inspection device such as the ultrasonic echo diagnostic device (an ultrasound diagnostic apparatus, an ultrasonic image apparatus) is described by using FIGS. 10 and 11. FIG. 10 is a perspective view illustrating the ultrasonic echo diagnostic device including the ultrasonic probe of this embodiment. FIG. 11 is a schematic view illustrating the ultrasonic probe of this embodiment.

The ultrasonic echo diagnostic device is a diagnostic device for medical use which uses the permeability of sound waves such that the inside of the living body which is invisible from the outside is imaged in real time to be visualized by using the ultrasonic waves exceeding an audible range. As illustrated in FIG. 10, the ultrasonic echo diagnostic device 130 includes a main body 132, a display part 133 which is provided above the main body 132, an operation part 136 attached in the front surface portion of the main body, and an ultrasonic probe (ultrasonic probe) 11 including the chip CHP1. A cable (cord) 138 extends from the ultrasonic probe 11, and the cord is connected to the main body 132 in a connection part 137. The operation part 136 is input equipment such as a track ball, a keyboard, or a mouse or a combination of them. The display part 133 is a display device for displaying an image-processed diagnostic image.

In the chip CHP1, the AC voltage and the DC voltage are supplied from a transmission amplifier AMP2 on the main body 132 side and the DC bias power source DC through the cable 138. The ultrasonic probe 11 illustrated in FIG. 11 is a transmitting/receiving part of ultrasonic waves. The chip CHP1 is attached on the tip surface of the probe case configuring the ultrasonic probe 11 in a state where the principal surface (a surface where the plurality of vibrators are formed) thereof is directed outward.

The surface of the chip CHP1 may be covered with a coating layer so as to protect the cell array CA from being damaged and to efficiently transmit the ultrasonic waves to the object (living body). The coating layer may have a cross section of a convex lens shape to serve as an acoustic lens for converging ultrasonic waves. A material such as silicone rubber, soft urethane resin, or elastomer can be used for the coating layer or the acoustic lens. It is desirable that a material which first has an electrical insulation and secondly has an acoustic impedance similar to that of the object is selected for the material of the coating layer.

In the ultrasonic diagnosis, after the tip of the ultrasonic probe 11 abuts on the surface of the object, scanning is performed while gradually shifting the position where the tip of the ultrasonic probe 11 abuts on the surface of the subject. At that time, the ultrasonic pulses of several MHz are transmitted into the object from the ultrasonic probe 11 close to the body surface, and reflected waves (echo) from the tissue boundary different in acoustic impedance are received. Accordingly, the tomographic image of the living tissue which is displayed on the display part 133 illustrated in FIG. 10 can be obtained to notify information on a diagnostic target. The distance information of a reflector is obtained by the time interval from the transmission to the reception of the ultrasonic waves. In addition, the information on the presence or quality of the reflector is obtained from the level or outline of the reflected waves.

As illustrated in FIG. 11, the plurality of printed substrates are mounted in the ultrasonic probe 11. For example, the plurality of printed substrates in the ultrasonic probe 11 include the substrate AMP in which the amplifying circuit AMP1 illustrated in FIG. 5 is mounted and the substrate CN in which the connector circuit connecting the amplifying circuit AMP1 and the ultrasonic echo diagnostic device 130 (see FIG. 9) is mounted.

The substrates AMP and CN may be printed substrates different from each other or may be one printed substrate. FIG. 11 illustrates the substrates AMP and CN side by side. However, the substrates may be overlapped in the ultrasonic probe 11 in the thickness direction.

In this embodiment, as illustrated in FIGS. 2 and 3, the resistance element R1 and the capacitor C1 as a DC block capacitor are mounted together in the chip CHP1 in which the cells of the CMUT are mounted. Accordingly, it is not required that, as in the comparative example illustrated in FIG. 12, the resistance element as a passive component and the block capacitor as a passive component are provided, and the printed substrate mounted with the passive components is arranged in the ultrasonic probe 11 similarly to the substrate AMP or the like. Thus, the ultrasonic probe 11 can be miniaturized. That is, the performance of the ultrasonic probe 11 can be improved.

Hereinbefore, the invention made by the inventor has been described based on the embodiments. However, the invention is not limited to the embodiments. The detailed configuration can be changed variously in a range without departing from the gist of the invention.

For example, in the first and second embodiments, the description is given about a case where the ultrasonic transducer array and the ultrasonic probe are used as a diagnostic device for medical use to be brought close to the surface of the living body or the like. However, the ultrasonic transducer array and the ultrasonic probe described in the first and second embodiments can be used in various ultrasonic inspection devices such as a catheter, a microscope, and an industrial nondestructive inspection device.

What is claimed is:
1. An ultrasonic transducer array comprising:
a substrate;
a first electrode which is formed above the substrate and extends along an upper surface of the substrate in a first direction;
a second electrode which is formed above the substrate and extends in a second direction orthogonal to the first direction in plan view;
a third electrode which is formed above the substrate under the first electrode and the second electrode and extends in the first direction;
a fourth electrode which is formed above the substrate under the first electrode and the second electrode and extends in the first direction; and
a first gap which is formed between the first electrode and the second electrode in a first area where a part of the first electrode and a part of the second electrode are overlapped with each other in plan view, wherein
the third electrode and the fourth electrode overlapped with each other in plan view configure a first capacitor,
the first electrode, the second electrode, and the first gap overlapped with each other in plan view configure an ultrasonic wave vibrator consisting of a second capacitor, and
a planar shape of each of the first electrode, the second electrode, the third electrode, and the fourth electrode is a rectangle shape.

2. The ultrasonic transducer array according to claim 1, wherein
the first capacitor is not vibrated acoustically.

3. The ultrasonic transducer array according to claim 1, further comprising:
a wiring which is arranged in parallel with the second electrode in the first direction and extends in the second direction; and
a resistance element of which one end is connected with the first electrode, and another end is electrically connected to the wiring, wherein
the wiring is electrically connected to a DC power source.

4. The ultrasonic transducer array according to claim 1, wherein
a part of the first capacitor is overlapped with the first area, and another part of the first capacitor extends in a peripheral area of not being overlapped with the first area in plan view in the first direction.

5. The ultrasonic transducer array according to claim 4, wherein
a part of the first capacitor is positioned just under a bonding pad formed in the peripheral area.

6. The ultrasonic transducer array according to claim 3, wherein
the resistance element is integrated with the first electrode and has a cross-sectional area smaller than that of the first electrode.

7. The ultrasonic transducer array according to claim 3, wherein
the plural first electrodes, the plural third electrodes, the plural fourth electrodes, and the plural resistance elements are arranged in parallel in the second direction, and
each of the plural first electrodes are electrically connected to the wiring through the plural resistance elements.

8. The ultrasonic transducer array according to claim 1, wherein
the second electrode is electrically connected to a negative terminal of a DC power source,
the third electrode is electrically connected to each of a positive side terminal of the DC power source and the first electrode, and
the fourth electrode is electrically connected to an amplifying circuit.

9. The ultrasonic transducer array according to claim 8, wherein the third electrode or the fourth electrode is electrically connected to a driving signal source which supplies a voltage to the second capacitor when ultrasonic waves are oscillated by the ultrasonic wave vibrator.

10. The ultrasonic transducer array according to claim 1, wherein the plural first capacitors are formed to be overlapped in a vertical direction, and the plural first capacitors are connected in parallel with each other.

11. The ultrasonic transducer array according to claim 1, wherein a second gap is formed between the third electrode and the fourth electrode.

12. An ultrasonic probe comprising:

the ultrasonic transducer array according to claim 1.

\* \* \* \* \*